(12) United States Patent
Bettarini et al.

(10) Patent No.: US 6,329,323 B1
(45) Date of Patent: Dec. 11, 2001

(54) AMINOSULFONYLUREAS WITH HERBICIDAL ACTIVITY

(75) Inventors: Franco Bettarini, Novara; Sergio Massimini, Bollate-Milan; Giovanni Meazza, Saronno-Varese; Giampaolo Zanardi, Novara; Domenico Portoso, Lodi; Ernesto Signorini, Malnate-Varese, all of (IT)

(73) Assignee: Isagro Ricerca S.r.l., Milan (IT)

( * ) Notice: Subject to any disclaimer, the term of this patent is extended or adjusted under 35 U.S.C. 154(b) by 0 days.

(21) Appl. No.: 09/380,592

(22) PCT Filed: Mar. 9, 1998

(86) PCT No.: PCT/EP98/01417

§ 371 Date: Oct. 21, 1999

§ 102(e) Date: Oct. 21, 1999

(87) PCT Pub. No.: WO98/40361

PCT Pub. Date: Sep. 17, 1998

(30) Foreign Application Priority Data

Mar. 13, 1997 (IT) .............................. MI97A0554

(51) Int. Cl.[7] ........................ A01N 45/54; C07D 239/42; C07D 239/69
(52) U.S. Cl. .................. 504/214; 544/321; 544/323; 544/332
(58) Field of Search .................. 504/214; 544/332, 544/321, 323

(56) References Cited

U.S. PATENT DOCUMENTS 4,696,695 * 9/1987 Gemert ................................. 544/332

FOREIGN PATENT DOCUMENTS 44 14 840 A1    11/1995   (DE) .

* cited by examiner

*Primary Examiner*—John M. Ford
(74) *Attorney, Agent, or Firm*—Oblon, Spivak, McClelland, Maier & Neustadt, P.C.

(57) ABSTRACT

This invention relates to aminosulfonylureas possessing a high herbicidal activity, a process for their preparation and their application to control control weeds in agriculture. Aminosulfonylureas of this invention have the following formula (I):

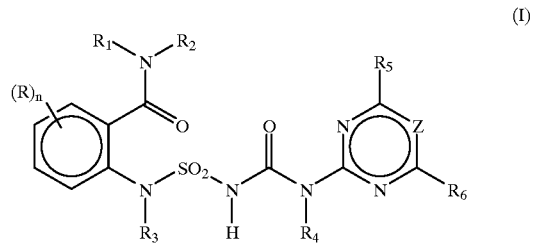

wherein R, $R_1$, $R_2$, $R_3$, $R_4$, $R_5$, and $R_6$ are described in the specification.

8 Claims, No Drawings

AMINOSULFONYLUREAS WITH HERBICIDAL ACTIVITY

This invention relates to aminosulfonylureas.

More in particular, this invention relates to aminosulfonylureas possessing a high herbicidal activity, a process for their preparation and their application as herbicides for controlling weeds in agricultural cultures. Aminosulfonylureas with herbicidal activity have, among other things, been described in the U.S. Pat. Nos. 4,515,620, 4,559,081, 4,592,776, 4,622,065 and 4,666,508. However, these products turn out to have a very poor selectivity while generally being toxic to the most important agricultural cultures.

The applicant has now discovered new aminosulfonylureas which have a higher herbicidal activity against numerous weeds, exhibiting at the same time a low phytotoxicity to one or more of the cultivations of prime agricultural interest. Therefore, they have a higher cell selectivity.

The object of this invention are thus aminosulfonylureas of the following general formula (I):

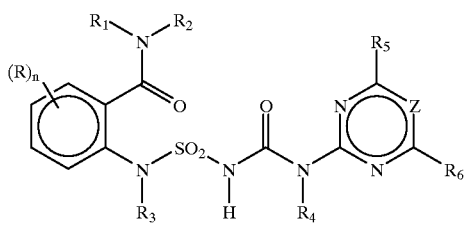

in which:
- R represents a halogen atom such as chlorine, fluorine, bromine or iodine; an alkylic or haloalkylic linear or branched $C_1$–$C_4$ group; an alkoxylic or haloalkoxylic linear or branched $C_1$–$C_4$ group;
- N represents 0 or 1;
- $R_1$ and $R_2$, equal or different from each other, represent an atom of hydrogen; an alkylic or haloalkylic linear or branched $C_1$–$C_4$ group; an alkoxylic or haloalkoxylic linear or branched $C_1$–$C_4$ group; or, jointly, an alkylenic or oxyalkylenic $C_2$–$C_5$ chain;
- $R_3$ and $R_4$, equal or different from each other, represent an atom of hydrogen; an alkylic or haloalkylic linear or branched $C_1$–$C_4$ group; an alkoxyalkylic or haloalkoxyalkylic linear or branched $C_3$–$C_6$ group; an alkenylic or haloalkenylic linear or branched $C_3$–$C_6$ group; an alkynylic or haloalkynylic linear or branched $C_3$–$C_6$ group;
- $R_5$ and $R_6$, equal or different from each other, represent an atom of hydrogen; a halogen atom such as chlorine, fluorine, bromine or iodine; an alkylic or haloalkylic linear or branched $C_1$–$C_6$ group; an alkylaminic linear or branched $C_1$–$C_6$ group; a dialkylaminic linear or branched $C_2$–$C_8$ group; a cycloalkylic or cycloalkoxylic $C_3$–$C_6$ group; a cycloalkylalkylic or cycloalkylalcoxylic $C_4$–$C_7$ group;
- Z represents CH or N.

The aminosulfonylureas of the general formula (I) are endowed with high herbicidal activity. Specific examples of aminosulfonylureas having the general formula (I) which are interesting for their herbicidal activity are:
2-[(4,6-dimethoxypyrimidin-2-yl)carbamoylsulfamoylamino]-N,N-dimethyl- benzamide;
1-[(4,6-dimethoxypyrimidin-2-yl)-3-{[2-(1-pyrrolidinocarbonyl)phenyl]sulfamoyl}urea,
2-[(4,6-dimethoxypyrimidin-2-yl)carbamoylsulfamoylamino]-N-ethyl-N-methylbenzamide;
2-[(4,6-dimethoxypyrimidin-2-yl)carbamoylsulfamoylamino]-N-methylbenzamide;
2-[(4,6-dimethoxypyrimidin-2-yl)carbamoylsulfamoylamino]-N-ethylbenzamide;
2-[(4,6-dimethoxypyrimidin-2-yl)carbamoylsulfamoylamino]-N-methoxybenzamide;
2-[(4,6-dimethoxypyrimidin-2-yl)carbamoylsulfamoylamino]-N-methoxy-N-methylbenzamide;
2-[(4,6-dimethoxypyrimidin-2-yl)carbamoylsulfamoylamino]benzamide;
2-[(4,6-dimethoxypyrimidin-2-yl)carbamoylsulfamoylmethylamino]-N,N-dimethylbenzamide;
N-cyclopropyl-2-[(4,6-dimethoxypyrimidin-2-yl)carbamoylsulfamoylamino]- benzamide;
2-[(4,6-dimethoxypyrimidin-2-yl)carbamoylsulfamoylamino]-N-(2,2,2-trifluoroethyl)benzamide;
4-chloro-6-[(4,6-dimethoxypyrimidin-2-yl)carbamoylsulfamoylamino]-N,N-dimethylbenzamide;
3-chloro-6-[(4,6-dimethoxypyrimidin-2-yl)carbamoylsulfamoylamino]-N,N-dimethylbenzamide;
2-[(4,6-dimethoxypyrimidin-2-yl)carbamoylsulfamoylamino]-5-fluoro-N,N-dimethylbenzamide;
2-[(4,6-dimethoxypyrimidin-2-yl)carbamoylsulfamoylamino]-6-fluoro-N,N-dimethylbenzamide;
2-[(4,6-dimethoxypyrimidin-2-yl)carbamoylsulfamoylamino]-5-methyl-N,N-dimethylbenzamide;
2-[(4,6-dimethoxypyrimidin-2-yl)carbamoylsulfamoylamino]-6-methyl-N,N-dimethylbenzamide;
N,N-dimethyl-2-[(4-methoxy-6-methylpyridin-2-yl)carbamoylsulfamoylamino]-benzamide;
N,N-dimethyl-2-[(4-methoxy-6-methylpyrimidin-2-yl)carbamoylsulfamoylamino]-benzamide.
N,N-dimethyl-2-[(4,6-dimethylpyrimidin-2-yl)carbamoylsulfamoylamino] benzamide.

The aminosulfonylureas having the general formula (I) of the present invention have an acidic nature and can therefore form salts with basic substances such as, for example, alkaline metal and alkaline earth hydroxides, amines and other organic bases, and quaternary amine salts.

The aminosulfonylureas having the general formula (I) in their salified form also fall within the scope of this invention and therefore constitute a further object of the same.

A further object of this invention is a process for the preparation of compounds having the general formula (I). The compounds having the general formula (I) may be obtained by a process including:

(a) reacting a heterocyclic amine having the general formula (II):

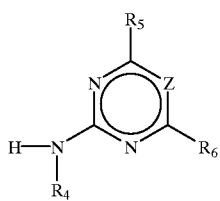

(II)

in which $R_4$, $R_5$, $R_6$, and Z have the meanings as described above, with a halosulfonylisocyanate having the general formula (III):

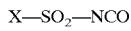

X—SO$_2$—NCO    (III)

in which X represents a halogen atom such as, for instance, chlorine, fluorine, or bromine, preferably chlorine, in the presence of an inert organic solvent, whereby a halosulfamoylurea of the following general formula (IV) is obtained:

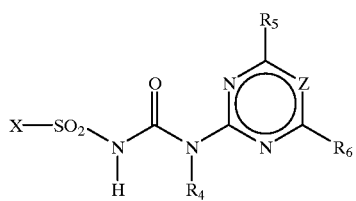

(IV)

in which X, $R_4$, $R_5$, $R_6$, and Z have the meanings as described above;

(b) reacting of halosulfamoylurea having the general formula (IV) obtained in the step (a) with an aniline having the general formula (V):

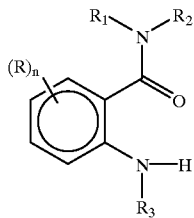

(V)

in which R, $R_1$, $R_2$, and $R_3$ have the same meanings described above, in the presence or absence of a base, preferably in the presence of a base, and of an inert organic solvent.

The inert organic solvents useful in the steps (a) and (b) of the process described above are aromatic hydrocarbons (such as for example benzene, toluene, xylene, etc.), chlorinated hydrocarbons (such as for example, methylene chloride, chloroform, carbon tetrachloride, chlorobenzene etc.), and ethers (such as, for example, ethyl ether, dimethoxyethane, tetrahydrofurane, dioxane, etc.).

The bases useful in the step (b) of the process described above are organic bases, preferably aliphatic amines such as, for example, triethylamine, etc.

The subject reaction steps (a) and (b) are performed at temperatures between −70° C. and the boiling temperature of the solvent employed, preferably between −20° C. and +30° C. The reaction of step (b), between aniline having the general formula (V) and halosulfamoylurea having the general formula (IV), may be conveniently performed without isolating said halosulfamoylurea (IV), by adding the aniline (V) and the base (diluted with the same inert organic solvent used in the step (a) of the above process), while operating in the same ambient in which the first passage was performed.

The heterocyclic amines having the general formula (II) and the halosulfonylisocyanates having the general formula (III) are compounds known in the art.

The anilines having the general formula (V) can, if not already known on their own, be prepared according to the methods known in the art.

The compounds having the general formula (I), objects of this invention, have evidenced interesting biological activities and, in particular, a high herbicidal activity which renders them suitable for use in the agricultural field to defend the useful cultures from weeds.

In particular, the compounds having the general formula (I) are effective in controlling, both before and after an emergency, numerous cotyledon and dicotyledon weeds. At the same time, these compounds show a compatibility or absence of toxic effects toward useful cultures, both while treating before and after emergence.

Examples of weeds effectively controlled by using the compounds having the general formula (I) as the object of this invention are: *Abutilon theofrasti, Amaranthus retroflexus, Amni maius, Capsella bursa pastoris, Chenopodium Album, Convolvulus sepium, Galium Aparine, Geranium dicotomiflorum,* Ipomea spp., Matricaria spp, *Papaver rhoeas, Portulaca oleracea, Sida spinosa, Solanum nigrum, Stellaria media, Alopecurus myosuroides, Digitaria sanguinalis,* Echinocloa spp., Scirpus spp., Cyperus spp., etc.

At the usage dosages useful for agricultural applications, the above compounds have not evidenced toxic effects towards important agricultural cultures such as rice (*Oryza sativa*), wheat (Triticum spp.), corn (*Zea mais*), soya (*Glycine max*), etc.

A further object of this invention is a method to control weeds in cultured areas, by applying the compounds having the general formula (I).

The quantity of a compound needed to achieve the desired result may vary depending on a number of factors such as, for instance, the compound to be used, the culture to be preserved, the weed to be attacked, the degree of infestation, the weather conditions, the characteristics of the soil, the method of application, etc.

Dosages of the compound in the range from 1 g to 1,000 g per hectare generally provide adequate control.

For practical applications in agriculture it is often beneficial to utilize compositions with a herbicidal activity containing, as an active substance, one or more compounds of the general formula (I), eventually also in a mixture with isomers, both in a free or in a salified form.

It is possible to use compounds presenting themselves in the form of dry powders, wettable powders, emulsifyable concentrates, microemulsions, pastes, granulates, solutions, suspensions, etc.: the choice of the type of composition will depend on the specific application.

The compositions are prepared according to known methods, for example by diluting or solving the active substance in a solvent and/or solid medium, eventually in the presence of surfactants.

The substances to be used as solid inert diluents or supports may be caoline, alumina, silica, talc, bentonite, gypsum, quartz, dolomite, attapulgite, montmorillonite, diatomaceous earth, cellulose, starch, etc.

The substances to be used as inert liquid diluents may, in addition to water, be organic solvents such as aromatic hydrocarbons (xylene, blends of alkylbenzenes, etc.), aliphatic hydrocarbons (hexane, cyclohexane, etc.), aromatic halogenated hydrocarbons (chlorobenzene, etc.), alcohols (methanol, propanol, butanol, octanol, etc.) esters (isobutylacetate, etc.), ketones (acetone, cyclohexanone, acetophenone, isoforone, ethylamylketone, etc.), vegetable and mineral oils and their mixtures, etc.

As surfactants certain wetting and emulsifying agents may be used having a non-ionic character (polyethoxylated alkylphenols, polyethxylated fatty alcohols, etc.), an anionic character (alkylbenzenesulfonates, alkylsulfonates,etc.), a cationic character quaternary alkylammonium salts, etc.).

It may also be possible to add dispersants (for example lignin and its salts, cellulose derivatives, alginates, etc.), stabilizers (for example antioxidants, ultraviolet ray absorbers, etc.).

To increase the range of action of the above compositions, other active ingredients can also be added such as, for example, other herbicides, fungicides, insecticides or acaricides, and fertilizers. Examples of other herbicides which can be added to the compositions containing one or more compounds of the general formula (I) are the following:

Acetochlor, acifluorfen, aclonifen, AKH-7088, alachlor, alloxydim, ametryn, amidosulfuron, amicrole, anilofos, asulam, atrazine, azafenidin (DPX-R6447), azimsulfuron (DPX-A8947), aziprotrine, benazolin, benfluralin, benfuresate, bensulfuron, bensulide, bentazone, benzofenap, benzthiazuron, bifenox, bilanafos, bispyribac-sodium (KIH-2023), bromacil, bromobutide, bromofenoxim, bromoxynil, butachlor, butamiphos, butenachlor, butralin, butroxydim, butylate, cafenstrole (CH-900), carbetamide, carfentrazone-ethyl (F-8426), chloromethoxyfen, chloramben, chlorbromuron, chlorbufam, chlorfurenol, chloridazon, chlorimuron, chlornitrofen, chlorotoluron, chloroxuron, chlorpropham, chlorsulforon, chlorthal, chlorthiamid, cinidon ethyl, cinmethylin, cinosulfuron, clethodim, chlodinafop, clomazone, clomeprop, clopyralid, chloransulam-methyl (XDE-565), cumyluron (JC-940), cyanazine, cycloate, cyclosulfamuron, (AC-322140), cycloxydim, cyhalofop-butyl (XDE-537), 2,4-D, 2,4-DB, daimuron, dalapon, desnedipham, desmetryn, dicamba, dichlobenil, dichlorprop, dichlorprop-P, diclofop, diclosulam (XDE-564), diethatyl, difenoxuron, difenzoquat, diflufenican, diflufenzopyr (SAN 835H), dimefuron, dimepiperate, dimethachlor, dimethametryn, dimethenamid, dinitramine, dinoseb, dinoseb acetate, dinotherb, diphenamid, dipropetryn, diquat, dithiopyr, 1-diuron, eglinazine, endothal, epoprodan (MK-243), EPTC, esprocarb, ethalfluralin, ethametsulfuron-methyl (DPX-A7881), ethidimuron, ethiozin (SMY 1500), ethofumesate, ethoxyfen-ethyl (HC-252), ethoxysulfuron (HOE 095404), ethobenzanid (HW 52), fenoxaprop, fenoxaprop-P, fentrazamide (BAY YRC 2388), fenuron, flamprop, flamprop-M, flazasulfuron, fluazifop, fluazifop-P, fluchloralin, flumetsulam (DE-498), flumiclorac-pentyl, flumioxazin, flumipropin, flumeturon, fluoroglycofen, fluoronitrofen, flupoxam, flupropanate, flupyrsulfuron (DPX-KE459), flurenol, fluridone, flurochloridone, fluroxypyr, flurtamone, fluthiacet-methyl (KIH-9201), fluthiamide (BAY FOE 5043), fomesafen, fosamine, furyloxyfen, glufosinate, glyphosate, halosulfuron-methyl (NC-319), haloxyfop, haloxyphop-P-methyl, hexazinone, imazamethabenz, imazamox (AC-299263), imazapic (AC-263222), imazapyr, amazaquin, imazethapyr, imazosulfuron, ioxynil, isopropalin, isopropazol (JV 485), isoproturon, isouron, isoxaben, isoxaflutole (RPA 201772), isoxapyrifop, KPP-421, lactofen, lenacil, linuron, LS830556, MCPA, MCPA-thioethyl, MCPB, mecoprop, mecoprop-P, mefenacet, metamitron, metazachlor, methabenzthiazuron, methazole, methoprotryne, methyldymron, metobenzuron, metobromuron, metolachlor, metosulam (DE-511), metoxuron, metribuzin, metsulfuron, molinate, monalide, monolinuron, naproanilide, napropamide, naptalam, NC-330, neburon, nicosulfuron, nipyraclofen, norflurazon, orbencarb, oryzalin, oxadiargyl, oxadiazon, oxasulfuron (CGA-277476), oxaziclomefone (MY-100), oxyfluorfen, paraquat, pebulate, pendimethalin, pentanochlor, pentoxazone (KPP-314), phenmedipham, picloram, piperophos, prenilachlor, primisulfuron, prodiamine, proglinazine, prometon, prometryne, propachlor, propanil, propaquizafop, propazine, propham, propisochlor, propyzamide, prosulfocarb, prosulfuron (CGA-152005), pyraflufen-ethyl (ET-751), pyrazolynate, pyrazolsulfuron, pyrazoxyfen, pyribenzoxim (LGC-40863), pyributicarb, pyridate, pyriminobac-methyl (KIH-6127), pyrithiobac-sodium (KIH-2031), quinchlorac, quinmerac, quizalofop, quizalofop-P, rimasulfuron, sethoxydim, siduron, simazine, simetryn, sulcotrione, sulfentrazone (F6285), sulfometuron (DPX-5648, sulfosulfuron (MON 37500), 2,3,6-TBA, TCA-sodium, tebutam, tebuthiuron, tepraloxydim (BAS 620H), terbacil, terbumeton, terbuthyl-azine, terbutryn, therylchlor (NSK-850, thiazafluron, thiazopyr (MON 13200), thidiazimin, thifensulfuron, thioencarb, tiocarbazil, tioclorim, tralkoxydim, tri-allate, triasulfuron (CGA-131036), triaxiflam (IDH-1105), tribenuron, triclopyr, trietazine, trifluralin, triflusilfuron-methyl (DPX-66037), UBI-C4874, vernolate.

The concentration of active substance of the general formula (I) in the above compositions can vary within a wide range, depending on the active compound, the applications for which they are destined, the environmental conditions and the kind of formulation. The concentration of active substance is generally between 1% and 90%, preferably between 5 and 50%.

The following examples are illustrative and do not limit the scope of this invention.

EXAMPLE 1

Preparation of 2-[(4,6-dimethoxypyrimidin-2-yl) carbamoylsulfamoylamino]-N,N-dimethylbenzamide (Compound Nr.1)

Under a nitrogen atmosphere, chlorosulfonyl isocyanate (4.3 g; 30.5 mmoles) dissolved in methylene chloride (10 ml) are dropped into a solution of 2-amino-4,6-dimethoxypyrimidine (5.2 g; 33.6 mmoles) in methylene chloride (50 ml) at −5° C.

The mixture is stirred at 0° C. for 1 h. A solution of 2-amino-N,N-dimethylbenzamide (5 g; 30.5 mmoles) and triethylamine (3.1 g; 30.6 mmoles) in methylene chloride (20 ml) is then added and the mixture is stirred for 30 min at 0° C. and for further 3 hours at room temperature. The reaction mixture is poured into a 2 l. solution of brine and 1% aqueous HCl and extracted with methylene chloride. The organic phase is washed with brine, dried with sodium sulfate and concentrated at reduced pressure. The residue (12.8 g) is stirred at 50° C. with ethyl acetate (20 ml); after cooling the solid is filtered and washed with diethyl ether. The desired product (11.3 g) has a melting point at 160–162° C.

EXAMPLE 2

Operating analogously to what is described in example 1, the following compounds have been prepared, starting from the appropriate 2-aminopyrimidines and 2-aminobenzamides:

1-(4,6-dimethoxypyrimidin-2-yl)-3-{[2-(1-pyrrolidinocarbonyl)phenyl]sulfa-moyl}urea (Compound Nr. 2): m.p. 154–1560° C.;

2-(4,6-dimethoxypyrimidin-2-yl) carbamoylsulfamoylamino]-N-ethyl-N-methylbenzamide (Compound Nr. 3): m.p. 136–138° C.;

2-(4,6-dimethoxypyrimidin-2-yl) carbamoylsulfamoylamino]-N-methylbenzamide (Compound Nr. 4): m.p. 98–100° C.;

2-(4,6-dimethoxypyrimidin-2-yl) carbamoylsulfamoylamino]-N-ethylbenzamide (Compound Nr. 5): m.p. 98–100° C.;

2-(4,6-dimethoxypyrimidin-2-yl) carbamoylsulfamoylamino]-N-methoxybenzamide (Compound Nr. 6): m.p. 147–149° C.;

2-(4,6-dimethoxypyrimidin-2-yl) carbamoylsulfamoylamino]-N-methoxy-N-methylbenzamide (Compound Nr. 7): m.p. 137–139° C.;

2-(4,6-dimethoxypyrimidin-2-yl) carbamoylsulfamoylamino]benzamide (Compound Nr. 8): m.p. 164–166° C.;

2-(4,6-dimethoxypyrimidin-2-yl) carbamoylsulfamoylmethylamino]-N,N-dimethylbenzamide (Compound Nr. 9): m.p. 120–121° C.;

N-cyclopropyl-2-(4,6-dimethoxypyrimidin-2-yl) carbamoylsulfamoylamino) benzamide (Compound Nr. 10) -2-(4,6-dimethoxypyrimidin-2-yl) carbamoylsulfamoylamino]-N-(2,2,2-trifluoroethyl)-benzamide (Compound Nr. 11) -4-chloro-6-[(4,6-dimethoxypyrimidin-2-yl) carbamoylsulfamoylamino]-N,N-dimethylbenzamide (Compound Nr. 12): m.p. 161–163° C.;

3-chloro-6-[(4,6-dimethoxypyrimidin-2-yl) carbamoylsulfamoylamino]-N,N-dimethylbenzamide (Compound Nr. 13): m.p. 156–158° C.;

2-(4,6-dimethoxypyrimidin-2-yl) carbamoylsulfamoylamino]-5-fluoro-N,N-dimethylbenzamide (Compound Nr. 14): m.p. 171–173° C.;

2-(4,6-dimethoxypyrimidin-2-yl) carbamoyisulfamoylamino]-6-fluoro-N,N-dimethylbenzamide (Compound Nr. 15): m.p. 165–167° C.;

2-(4,6-dimethoxypyrimidin-2-yl) carbamoylsulfamoylamino]5-methyl-N,N-dimethylbenzamide (Compound Nr. 16): m.p. 164–166° C.;

2-(4,6-dimethoxypyrimidin-2-yl) carbamoylsulfamoylamino]-6-methyl-N,N-dimethylbenzamide (Compound Nr. 17): m.p. 169–171° C.;

N,N-dimethyl-2-[(4-methoxy-6-methylpyrimidin-2-yl) carbamoylsulfamoylamino]-benzamide (Compound Nr. 18): m.p. 147–149° C.;

N,N-dimethyl-2-[(4,6-dimethylpyrimidin-2-yl) carbamoylsulfamoylamino]-benzamide (Compound Nr. 19):

m.p. 163–165° C.

EXAMPLE 3

Preparation of 2-[(4,6-dimethoxypyrimidin-2-yl) carbamoylsulfamoylami-no]-N,N-dimethylbenzamide monosodium salt (Compound Nr.20)

Crushed sodium hydroxide (400 mg; 10 mmoles) is added to a solution of Compound Nr.1 (Example 1; 4.25 g; 10 mmoles) in 100 ml of dichloromethane.

The mixture is stirred at room temperature for 18 h and concentrated under reduced pressure. The solid residue (4.3 g) has a melting point at 190° C.

EXAMPLE 4

Determination of the Herbicidal Activity and Phytotoxicity.

The herbicidal activity of Compounds Nr. 1, 2 and 4 with respect to some important weeds and the phytotoxicity with respect to wheat were evaluated, in post-emergence treatment, compared to 1-[(4,6-dimethoxypyrimidin-2-yl)-3-[(2-methoxycarbonylphenyl)sulfamoyl]urea described in the example 2 of the US-patent 4,515,620 (RC).

For each compound, the evaluation tests were carried out according to the following operating procedures.

Jars (diameter 10 cm, height 10 cm) containing sandy earth were prepared. In each of them, one of the following plant species was sown:

Weeds: *Abutilon theophrasti* (ABUTH), *Amaranthus retroflexus* (AMARE), *Amni maius* (MNMA), *Convolvulus sepium* (CONSE), *Galium Aparine* (GALAP), *Ipomea Purpurea* (IPOPU), *Papaver rhoeas* (PAPRH), *Solanum nigrum* (SOLNI);

Crops: *Triticum sp.* (Wheat).

To each jar, water was added in a suitable amount for a good germination of the seeds. The jars were divided into two groups each containing at least 5 jars for each weed. The first group was not treated with the compound under evaluation and was used as a comparison (control).

The second group of jars was treated, 15 days after sowing for the weeds and 10 days after sowing for wheat, with a hydroacetonic dispersion (20% by volume of acetone) containing the compound under testing at the desired rate and Tween 20 (0.5%).

All jars were kept under observation in a conditioned environment with the following conditions:

temperature: 24° C.

relative humidity: 60% photoperiod: 16 hours light intensity: 10,000 lux

Every two days the jars were uniformly watered to ensure a sufficient degree of humidity for a good development of the plants.

Twentyone days after the treatment, the herbicidal activity was evaluated on the basis of the following scale of values referring to the percentage of damage found on the plants which had been treated, compared to those not treated (control):

0=0%–9% of damage

1=10%–29% of damage

2=30%–49% of damage

3=50%–69% of damage

4=70%–89% of damage

5=90% of damage—death of plant

The results obtained are as shown in Table 1 below.

TABLE 1

| | | Herbicidal activity in post-emergence | | | |
|---|---|---|---|---|---|
| WEED/CROP | COMPOUND Rate (g/ha) | Nr.1 150-50 | Nr.2 150-50 | Nr.4 150-50 | RC 150-50 |
| ABUTH | | 5-3 | 4-2 | 5-3 | 5-2 |
| AMARE | | 5-3 | 1-0 | 5-4 | 3-1 |
| AMNMA | | 4-3 | 4-3 | 5-4 | 2-1 |
| CONSE | | 5-5 | 5-5 | 5-nt | 3-1 |
| GALAP | | 5-3 | 4-1 | 5-4 | 4-2 |
| IPOPU | | 5-3 | nt-nt | 5-4 | nt-0 |
| PAPRH | | 5-4 | 5-4 | nt-nt | nt-0 |
| SOLNI | | 5-3 | 3-2 | nt-nt | nt-0 |
| WHEAT | | 0-0 | 0-0 | 0-0 | 0-0 | nt = not tested.

What is claimed is:

1. A compound having the formula (I):

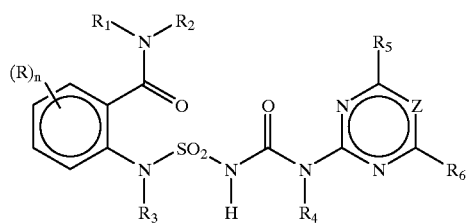

in which:

R represents a halogen atom; and alkyl or haloalkyl linear or branched $C_1$–$C_4$ group; and alkoxy or haloalkoxy linear or branched $C_1$–$C_4$ group;

n represents 0 or 1;

$R_1$ and $R_2$, equal or different from each other, represent hydrogen; and alkyl or haloalkyl linear or branched $C_1$–$C_4$ group; and alkoxy or haloalkoxy linear or branched $C_1$–$C_4$ group; or jointly an alkenyl or oxyalkenyl chain $C_2$–$C_5$;

$R_3$ and $R_4$, equal or different from each other, represent hydrogen; and alkyl or haloalkyl linear or branched $C_1$–$C_4$ group; and alkoxy or haloalkoxy linear or branched $C_3$–$C_6$ group; and alkenyl or haloalkenyl linear or branched $C_3$–$C_6$ group; and alkynyl or haloalkynyl linear or branched $C_3$–$C_6$ group;

$R_5$ and $R_6$, equal or different from each other, represent hydrogen; halogen; and alkyl or haloalkyl linear or branched $C_1$–$C_6$ group; and alkylamino linear or branched $C_1$–$C_6$ group; a dialkylamino linear or branched $C_2$–$C_8$ group; a cycloalkyl or cycloalkoxy $C_3$–$C_6$ group; a cycloalkylalkyl or cycloalkylalkoxy $C_4$–$C_7$ group;

Z represents—CH.

2. A compound according to claim 1 which is -2-(4,6-dimethoxypyrimidin-2-yl)carbamoylsulfamoylamino]-N,N-dimethylbenzamide.

3. A compound according to claim 1 which is -1-(4,6-dimethoxypyrimidin-2-yl)-3{[2-(1-pyrrolidinocarbonyl)phenyl]sulfamoyl}urea.

4. A compound according to claim 1 which is -2-(4,6-dimethoxypyrimidin-2-yl)carbamoylsulfamoylamino]-N-methylbenzamide.

5. A compound according to claim 1 which is -2-(4,6-dimethoxypyrimidin-2-yl)carbamoylsulfamoylamino]-N-ethylbenzamide.

6. A compound according to claim 1 which is -2-(4,6-dimethoxypyrimidin-2yl)carbamoylsulfamoylamino]-N-methoxybenzamide.

7. A compound according to claim 1 which is -2-(4,6-dimethoxypyrimidin-2-yl)carbamoylsulfamoylamino]-N-methoxy-N-methylbenzamide.

8. Alkali metal, alkaline earth metal, optionally alkylated ammonium or organic amine salts of compound, according to claim 1.

* * * * *